US010456400B2

(12) United States Patent
Lindsey et al.

(10) Patent No.: US 10,456,400 B2
(45) Date of Patent: Oct. 29, 2019

(54) AZA-ELLIPTICINE ANALOGS, METHODS OF SYNTHESIS AND METHODS OF TREATMENT

(71) Applicant: MUSC FOUNDATION FOR RESEARCH DEVELOPMENT, Charleston, SC (US)

(72) Inventors: Christopher C. Lindsey, Wadmalaw Island, SC (US); Craig C. Beeson, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 15/307,966

(22) PCT Filed: May 15, 2015

(86) PCT No.: PCT/US2015/030941
§ 371 (c)(1),
(2) Date: Oct. 31, 2016

(87) PCT Pub. No.: WO2015/179218
PCT Pub. Date: Nov. 26, 2015

(65) Prior Publication Data
US 2017/0081328 A1      Mar. 23, 2017

Related U.S. Application Data

(60) Provisional application No. 61/994,879, filed on May 17, 2014, provisional application No. 62/000,293, filed on May 19, 2014.

(51) Int. Cl.
*A61K 31/519* (2006.01)
*C07D 471/14* (2006.01)

(52) U.S. Cl.
CPC .......... *A61K 31/519* (2013.01); *C07D 471/14* (2013.01)

(58) Field of Classification Search
CPC ... A61K 31/519; C07D 403/14; C07D 471/14
USPC ....................................................... 514/287
See application file for complete search history.

(56) References Cited

U.S. PATENT DOCUMENTS

2009/0197906 A1   8/2009  Auclair et al.
2010/0249171 A1   9/2010  Ellies et al.

OTHER PUBLICATIONS

Zhang et al, J. Organic Chemistry (2000), vol. 65(23), pp. 7977-7983.*
Alajarin et al, J Nat Prod (1997) vol. 60, pp. 747-748. (Year: 1997).*
Bergman et al, Tetrahedron (2003), pp. 1033-1048. (Year: 2003).*
El Sayed et al, J Med. Chem. (2009), vol. 52, pp. 2979-2988. (Year: 2009).*
Haddadin et al, Organic Letters (2010), vol. 12 (23), pp. 5502-5505. (Year: 2010).*
James et al, Organic Letters (2008), vol. 10(6), pp. 1203-1206. (Year: 2008).*
Parvatkar et al, J Org. Chem. (2009), vol. 74, pp. 8369-8372. (Year: 2009).*
Patteux et al, Organic Letters (2003), vol. 5 (17), pp. 3061-3063 (Year: 2003).*
Schmittel et al, Angew. Chem Int. Ed. (2000), vol. 39(13), pp. 2152-2155. (Year: 2000).*
Voute et al, Org. Biomol. Chem. (2010), vol. 8, pp. 442-450. (Year: 2010).*
Thiel, Karl. Nature (2004), vol. 22(5), pp. 513-519. (Year: 2004).*
Anderson, Amy. Chemistry & Biology (2003), vol. 10, pp. 787-797. (Year: 2003).*
Zhang et al, J Org Chem (2000), vol. 65, pp. 7977-7983. (Year: 2000).*
Lu et al., "Synthesis of Novel Heteroaromatics Structurally Related to Ellipticine Alkaloids via Thermolysis of Pyridannulated Enyne-Carbodiimidee," J. Org. Chem. 2002, 67, 5412-5415.
The International Search Report and Written Opinion, dated Jul. 31, 2015, in the related PCT Application No. PCT/US15/30941.
Zhang et al. "Synthesis of 6H-Indolo[2,3-b][1,6]naphthyridines and Related Compounds as the 5-Aza Analogues of Ellipticine Alkaloids," Journal of Organic Chemistry, 2000, vol. 65, pp. 7977-7983.
Yu et al, "Cascade Reaction of Isatins with Heterocyclic Ketene Aminals: Synthesis of midazopyrroloquinoline Derivatives," Organic Letters, 2011, vol. 13, pp. 4782-4785.
Lashgari et al., "Synthesis of heterocyclic compounds based on isatin through 1, 3-dipolar cycloaddition reactions," ARKIVOC, 2012, vol. (i), pp. 277-320.
The partial supplementary European search report with the provisional opinion, dated Nov. 17, 2017, in the related European Application No. 15795495.9.
Estel: "Synthesis of ortho-substituted aminopyridines. Metalation of pivaloylamino derivatives", J. Heterocyclic Chem., Jan. 1, 1989, pp. 105-112, XP055419491.
Wang et al: "Synthesis and in vitro antiproliferative activity of new 11-aminoalkylamino-substituted 5- and 6-indolo[2,3-]quinolines; structureactivity relationships of neocryptolepines and 6-methyl congeners", Bioorganic & Medicinal Chemistry, Pergamon, GB, vol. 20, No. 15, May 27, 2012, pp. 4820-4829, XP028428241.

(Continued)

*Primary Examiner* — Craig D Ricci
*Assistant Examiner* — Janet L. Coppins

(57) ABSTRACT

In some aspects, the present invention relates to aza-ellipticine compounds of the formula: wherein the variables are as defined herein. The application also provides novel methods of preparing aza-ellipticine compounds, methods of using the compounds, and pharmaceutical compositions thereof.

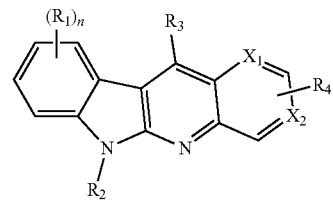

2 Claims, No Drawings

(56) References Cited

OTHER PUBLICATIONS

Chen Y-L et al: "Synthesis and anticancer evaluation of certain indolo[2,3-b]quinoline derivatives", Bioorganic & Medicinal Chemi, Pergamon, GB, vol. 12, No. 24, Dec. 15, 2004, pp. 6539-6546, XP004646494.

* cited by examiner

AZA-ELLIPTICINE ANALOGS, METHODS OF SYNTHESIS AND METHODS OF TREATMENT

CROSS-REFERENCE TO RELATED APPLICATIONS

This application is a National Stage Application of PCT/US2015/030941 filed on May 15, 2015, which claims priority from U.S. Provisional Patent Application No. 61/994,879 filed on May 17, 2014, and from U.S. Provisional Patent Application No. 62/000,293 filed on May 19, 2014. Each of prior mentioned applications is hereby expressly incorporated by reference herein in its entirety.

FIELD OF THE INVENTION

The present invention relates generally to the fields of chemistry, biology and medicine. More particularly, it concerns compounds, compositions and methods for the treatment and prevention of diseases such as cancer, HIV, and malaria.

All documents cited or relied upon below are expressly incorporated herein by reference.

BACKGROUND OF THE INVENTION

Elliptcine is a member of the pyrido[4,3-b]carbazole alkaloids that were first isolated from *Ochrosia elltica* Labill (Apocynaceae) in 1959. Approximately ten years later, the biological profile of these alkaloids has shown promise as potential antitumor compounds of interest demonstrating growth inhibition of various experimental tumors like S-180, adenocarcinoma-755, leukemia L-1210, and myeoblastic leukemia. 9-hydroxy-ellipticine, a CYP450 metabolite of ellipticine, serves as a particular analog of interest as it is forty times more potent than its parent (Ramkumar and Nagarajan, 2014). The pursuit of new synthetic analogs which exhibit greater potency has been hampered by a lack of appropriate simple synthetic methodologies to produce the analogs. Previous synthetic efforts have required multiple steps and are relatively low yielding (Zhang, et al., 2000). As such, new compounds and a straight forward synthetic methodology which allows the production of new compounds are needed.

SUMMARY OF THE INVENTION

The present disclosure provides novel compounds, methods of preparing aza-ellipticine and analogs thereof, methods of treatment and pharmaceutical compositions.

In one aspect, the present disclosure provides a compound of the formula:

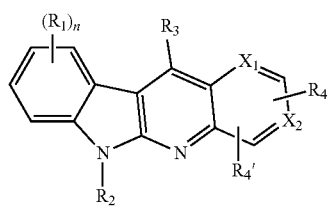
(I)

wherein: $R_1$ is hydrogen, hydroxy, halo, amino, carboxy, nitro, cyano, phosphate, sulfate, or $alkyl_{(C \leq 12)}$, $cycloalkyl_{(C \leq 12)}$, $alkenyl_{(C \leq 12)}$, $cycloalkenyl_{(C \leq 12)}$, $alkynyl_{(C \leq 12)}$, $aryl_{(C \leq 12)}$, $aralkyl_{(C \leq 12)}$, $heterocycloalkyl_{(C \leq 12)}$, $heteroaryl_{(C \leq 12)}$, $acyl_{(C \leq 12)}$, $amido_{(C \leq 12)}$, $alkoxy_{(C \leq 12)}$, $cycloalkoxy_{(C \leq 12)}$, $aryloxy_{(C \leq 12)}$, $aralkyloxy_{(C \leq 12)}$, $heterocycloalkyloxy_{(C \leq 12)}$, $heteroaryloxy_{(C \leq 12)}$, $alkylamino_{(C \leq 12)}$, $dialkylamino_{(C \leq 12)}$, $arylamino_{(C \leq 12)}$, $aralkylamino_{(C \leq 12)}$, or a substituted version of any of these groups; n is 0, 1, 2, 3, 4, or 5; $R_2$ is hydrogen, or $alkyl_{(C \leq 12)}$, $cycloalkyl_{(C \leq 12)}$, $alkenyl_{(C \leq 12)}$, $cycloalkenyl_{(C \leq 12)}$, $aryl_{(C \leq 12)}$, $acyl_{(C \leq 12)}$, or a substituted version of any of these groups; $R_3$, $R_4$, and $R_4'$ are each independently selected from hydrogen, halo, hydroxy, amino, or $alkyl_{(C \leq 12)}$, $cycloalkyl_{(C \leq 12)}$, $alkenyl_{(C \leq 12)}$, $cycloalkenyl_{(C \leq 12)}$, $aryl_{(C \leq 12)}$, $aralkyl_{(C \leq 12)}$, $heterocycloalkyl_{(C \leq 12)}$, $acyl_{(C \leq 12)}$, $alkoxy_{(C \leq 12)}$, $cycloalkoxy_{(C \leq 12)}$, $amido_{(C \leq 12)}$ or a substituted version of any of these groups; and $X_1$ and $X_2$ are each independently selected from =N— or =CR$_5$— wherein $R_5$ is hydrogen, halo, hydroxy, amino, $alkyl_{(C \leq 12)}$, $cycloalkyl_{(C \leq 12)}$, $aryl_{(C \leq 12)}$, $acyl_{(C \leq 12)}$, $alkoxy_{(C \leq 12)}$, $amido_{(C \leq 12)}$, substituted $alkyl_{(C \leq 12)}$, substituted $cycloalkyl_{(C \leq 12)}$, substituted $aryl_{(C \leq 12)}$, substituted $acyl_{(C \leq 12)}$, substituted $alkoxy_{(C \leq 12)}$, or substituted $amido_{(C \leq 12)}$; or a pharmaceutically acceptable salt or tautomer thereof. In some embodiments, the compound is further defined by the formula:

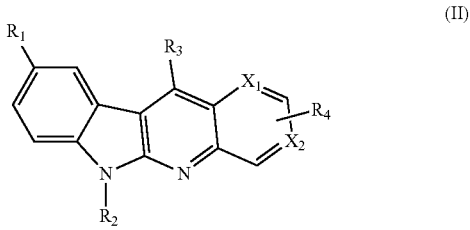
(II)

wherein: $R_1$ is hydrogen, hydroxy, halo, amino, carboxy, nitro, cyano, phosphate, sulfate, or $alkyl_{(C \leq 12)}$, $cycloalkyl_{(C \leq 12)}$, $alkenyl_{(C \leq 12)}$, $cycloalkenyl_{(C \leq 12)}$, $alkynyl_{(C \leq 12)}$, $aryl_{(C \leq 12)}$, $aralkyl_{(C \leq 12)}$, $heterocycloalkyl_{(C \leq 12)}$, $heteroaryl_{(C \leq 12)}$, $acyl_{(C \leq 12)}$, $amido_{(C \leq 12)}$, $alkoxy_{(C \leq 12)}$, $cycloalkoxy_{(C \leq 12)}$, $aryloxy_{(C \leq 12)}$, $aralkyloxy_{(C \leq 12)}$, $heterocycloalkyloxy_{(C \leq 12)}$, $heteroaryloxy_{(C \leq 12)}$, $alkylamino_{(C \leq 12)}$, $dialkylamino_{(C \leq 12)}$, $arylamino_{(C \leq 12)}$, $aralkylamino_{(C \leq 12)}$, or a substituted version of any of these groups; $R_2$ is hydrogen, or $cycloalkyl_{(C \leq 12)}$, $alkenyl_{(C \leq 12)}$, $cycloalkenyl_{(C \leq 12)}$, $aryl_{(C \leq 12)}$, $acyl_{(C \leq 12)}$, or a substituted version of any of these groups; $R_3$ and $R_4$ are each independently selected from hydrogen, halo, hydroxy, amino, or $alkyl_{(C \leq 12)}$, $cycloalkyl_{(C \leq 12)}$, $alkenyl_{(C \leq 12)}$, $cycloalkenyl_{(C \leq 12)}$, $aryl_{(C \leq 12)}$, $aralkyl_{(C \leq 12)}$, $heterocycloalkyl_{(C \leq 12)}$, $acyl_{(C \leq 12)}$, $alkoxy_{(C \leq 12)}$, $cycloalkoxy_{(C \leq 12)}$, $amido_{(C \leq 12)}$ or a substituted version of any of these groups; and $X_1$ and $X_2$ are each independently selected from =N— or =CR$_5$— wherein $R_5$ is hydrogen, halo, hydroxy, amino, $alkyl_{(C \leq 12)}$, $cycloalkyl_{(C \leq 12)}$, $aryl_{(C \leq 12)}$, $acyl_{(C \leq 12)}$, $alkoxy_{(C \leq 12)}$, $amido_{(C \leq 12)}$, substituted $alkyl_{(C \leq 12)}$, substituted $cycloalkyl_{(C \leq 12)}$, substituted $aryl_{(C \leq 12)}$, substituted $acyl_{(C \leq 12)}$, substituted $alkoxy_{(C \leq 12)}$, or substituted $amido_{(C \leq 12)}$; or a pharmaceutically acceptable salt or tautomer thereof. In some embodiments, the compound is further defined by the formula:

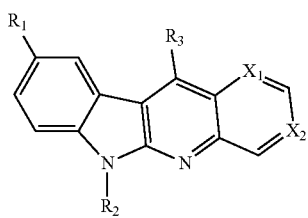

(III)

wherein: $R_1$ is hydrogen, hydroxy, halo, amino, carboxy, nitro, cyano, phosphate, sulfate, or alkyl$_{(C\leq12)}$, cycloalkyl$_{(C\leq12)}$, alkenyl$_{(C\leq12)}$, cycloalkenyl$_{(C\leq12)}$, alkynyl$_{(C\leq12)}$, aryl$_{(C\leq12)}$, aralkyl$_{(C\leq12)}$, heterocycloalkyl$_{(C\leq12)}$, heteroaryl$_{(C\leq12)}$, acyl$_{(C\leq12)}$, amido$_{(C\leq12)}$, alkoxy$_{(C\leq12)}$, cycloalkoxy$_{(C\leq12)}$, aryloxy$_{(C\leq12)}$, aralkyloxy$_{(C\leq12)}$, heterocycloalkyloxy$_{(C\leq12)}$, heteroaryloxy$_{(C\leq12)}$, alkylamino$_{(C\leq12)}$, dialkylamino$_{(C\leq12)}$, arylamino$_{(C\leq12)}$, aralkylamino$_{(C\leq12)}$, or a substituted version of any of these groups; $R_2$ is hydrogen, or alkyl$_{(C\leq12)}$, cycloalkyl$_{(C\leq12)}$, alkenyl$_{(C\leq12)}$, cycloalkenyl$_{(C\leq12)}$, aryl$_{(C\leq12)}$, acyl$_{(C\leq12)}$, or a substituted version of any of these groups; $R_3$ is hydrogen, halo, hydroxy, amino, or alkyl$_{(C\leq12)}$, cycloalkyl$_{(C\leq12)}$, alkenyl$_{(C\leq12)}$, cycloalkenyl$_{(C\leq12)}$, aryl$_{(C\leq12)}$, aralkyl$_{(C\leq12)}$, heterocycloalkyl$_{(C\leq12)}$, acyl$_{(C\leq12)}$, alkoxy$_{(C\leq12)}$, cycloalkoxy$_{(C\leq12)}$, amido$_{(C\leq12)}$ or a substituted version of any of these groups; and $X_1$ and $X_2$ are each independently selected from =N— or =CR$_5$— wherein $R_5$ is hydrogen, halo, hydroxy, amino, alkyl$_{(C\leq12)}$, cycloalkyl$_{(C\leq12)}$, aryl$_{(C\leq12)}$, acyl$_{(C\leq12)}$, alkoxy$_{(C\leq12)}$, amido$_{(C\leq12)}$, substituted alkyl$_{(C\leq12)}$, substituted cycloalkyl$_{(C\leq12)}$, substituted aryl$_{(C\leq12)}$, substituted acyl$_{(C\leq12)}$, substituted alkoxy$_{(C\leq12)}$, or substituted amido$_{(C\leq12)}$; or a pharmaceutically acceptable salt or tautomer thereof. In some embodiments, the compound is further defined by the formula:

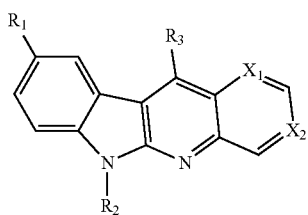

(III)

wherein: $R_1$ is hydrogen, hydroxy, halo, amino, or alkyl$_{(C\leq12)}$, cycloalkyl$_{(C\leq12)}$, alkoxy$_{(C\leq12)}$, cycloalkoxy$_{(C\leq12)}$, alkylamino$_{(C\leq12)}$, dialkylamino$_{(C\leq12)}$, arylamino$_{(C\leq12)}$, or a substituted version of any of these groups; $R_2$ is hydrogen, or alkyl$_{(C\leq12)}$, cycloalkyl$_{(C\leq12)}$, alkenyl$_{(C\leq12)}$, cycloalkenyl$_{(C\leq12)}$, aryl$_{(C\leq12)}$, acyl$_{(C\leq12)}$, or a substituted version of any of these groups; $R_3$ is hydrogen, halo, hydroxy, amino, or alkyl$_{(C\leq12)}$, cycloalkyl$_{(C\leq12)}$, alkoxy$_{(C\leq12)}$, cycloalkoxy$_{(C\leq12)}$ or a substituted version of any of these groups; and $X_1$ and $X_2$ are each independently selected from =N— or =CR$_5$— wherein $R_5$ is hydrogen, halo, hydroxy, alkyl$_{(C\leq12)}$, cycloalkyl$_{(C\leq12)}$, alkoxy$_{(C\leq12)}$, substituted alkyl$_{(C\leq12)}$, substituted cycloalkyl$_{(C\leq12)}$, or substituted alkoxy$_{(C\leq12)}$; or a pharmaceutically acceptable salt or tautomer thereof. In some embodiments, if $R_1$ and $R_2$ are both hydrogen, then $R_3$ is not alkyl$_{(C\leq6)}$, cycloalkyl$_{(C\leq6)}$, cycloalkenyl$_{(C\leq6)}$, or aryl$_{(C\leq12)}$. In some embodiments, if $R_3$ is alkyl$_{(C\leq6)}$, cycloalkyl$_{(C\leq6)}$, cycloalkenyl$_{(C\leq12)}$, or aryl$_{(C\leq12)}$, then $R_1$ or $R_2$ is not hydrogen. In some embodiments, $R_1$ is hydrogen. In other embodiments, $R_1$ is halo. In some embodiments, $R_1$ is chloro. In other embodiments, $R_1$ is alkoxy$_{(C\leq12)}$. In some embodiments, $R_1$ is methoxy. In other embodiments, $R_1$ is alkyl$_{(C\leq12)}$. In some embodiments, $R_1$ is alkyl$_{(C\leq6)}$. In some embodiments, $R_1$ is methyl. In some embodiments, $R_2$ is hydrogen. In other embodiments, $R_2$ is alkyl$_{(C\leq12)}$. In some embodiments, $R_2$ is alkyl$_{(C\leq6)}$. In some embodiments, $R_2$ is propyl. In some embodiments, $R_3$ is hydrogen. In other embodiments, $R_3$ is alkyl$_{(C\leq12)}$. In some embodiments, $R_3$ is alkyl$_{(C\leq6)}$. In some embodiments, $R_3$ is methyl. In some embodiments, the compound is selected from:

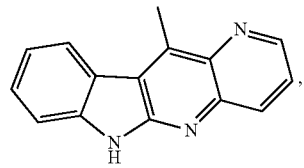

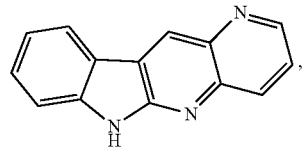

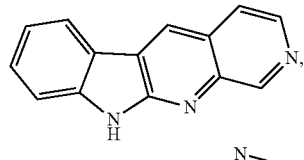

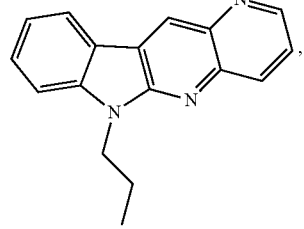

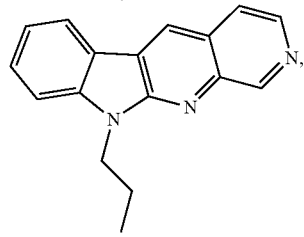

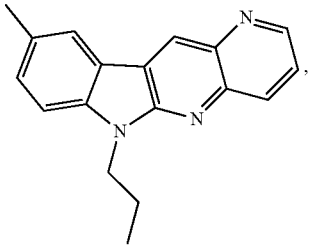

-continued

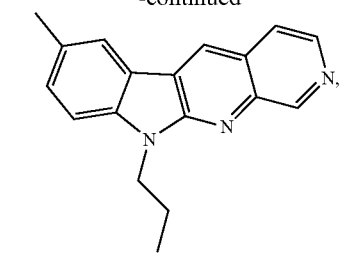

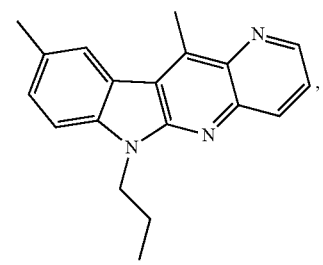

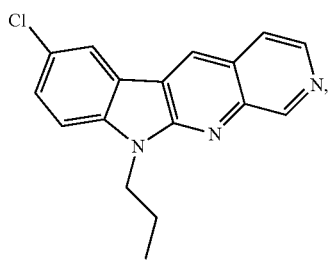

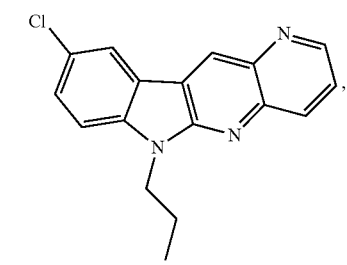

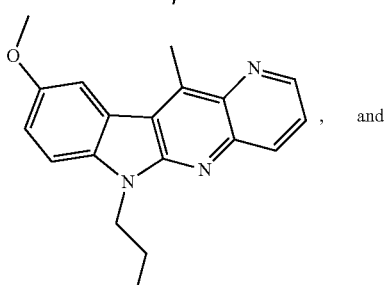
, and

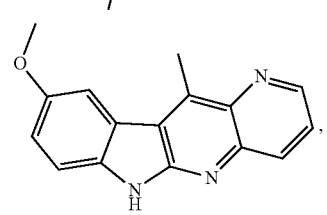

or a pharmaceutically acceptable salt or tautomer thereof.

In another embodiment of the present invention, provided is a compound of the formula I:

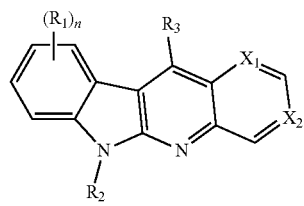

wherein:
R₁ is hydrogen, alkyl$_{(C\leq12)}$, alkoxy$_{(C\leq12)}$, halogen, hydroxy, —OC(O)CH₃ or —OCF₃;
n is 0 or 1;
R₂ is hydrogen, alkyl$_{(C\leq12)}$ or —C(O)CH₃;
R₃ is hydrogen or alkyl$_{(C\leq12)}$; and
X₁ and X₂ are each independently selected from =N or =C—; or
a pharmaceutically acceptable salt or tautomer thereof, wherein said compound is not 10H-indolo[2,3-b][1,7]naphthyridine.

In another aspect, the present disclosure provides a pharmaceutical composition comprising a compound of the present disclosure and an excipient.

In yet another aspect, the present disclosure provides a method of treating a disease comprising administering to a patient in need thereof a pharmaceutically effective dose of a compound of the present disclosure. In some embodiments, the disease is cancer. In some embodiments, the cancer is a carcinoma, sarcoma, lymphoma, leukemia, melanoma, mesothelioma, multiple myeloma, or seminoma. In some embodiments, the cancer is of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the cancer is leukemia or breast cancer. In some embodiments, the compound is administered with a second compound. In some embodiments, the second compound is a chemotherapeutic agent. In some embodiments, the chemotherapeutic agent is a platinum-based agent. In some embodiments, the platinum-based agent is cisplatin. In other embodiments, the chemotherapeutic is an antimitotic agent. In some embodiments, the antimitotic agent is doxorubicin, vincristine, paclitaxel, or 5-fluorouracil. In some embodiments, the method further comprises administering the compound with a second treatment. In some embodiments, the second treatment is surgery, radiation, or immunotherapy. In other embodiments, the disease is HIV. In some embodiments, the compound is administered with a second compound. In some embodiments, the second compound is anti-retroviral. In some embodiments, the anti-retroviral is a nucleoside/nucleotide reverse transcriptase inhibitor, non-nucleoside reverse transcriptase inhibitor, protease inhibitor, Example/fusion inhibitor, or integrase inhibitor. In other embodiments, the disease is malaria. In some embodiments, the compound is administered with a second compound. In some embodiments, the second compound is a quinine-based antimalarial, arteminsinins, sulfadoxine, or pyrimethanime. In some embodiments, the quinine-based anti-malarial is chloroquine and mefloquine.

In yet another aspect, the present disclosure provides a method of preparing a compound of the formula:

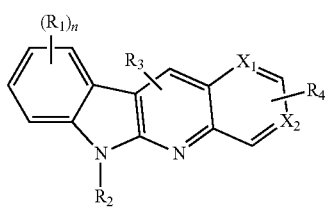

(IV)

wherein: $R_1$ is hydrogen, hydroxy, halo, amino, carboxy, nitro, cyano, phosphate, sulfate, or alkyl$_{(C\leq12)}$, cycloalkyl$_{(C\leq12)}$, alkenyl$_{(C\leq12)}$, cycloalkenyl$_{(C\leq12)}$, alkynyl$_{(C\leq12)}$, aryl$_{(C\leq12)}$, aralkyl$_{(C\leq12)}$, heterocycloalkyl$_{(C\leq12)}$, heteroaryl$_{(C\leq12)}$, acyl$_{(C\leq12)}$, amido$_{(C\leq12)}$, alkoxy$_{(C\leq12)}$, cycloalkoxy$_{(C\leq12)}$, aryloxy$_{(C\leq12)}$, aralkyloxy$_{(C\leq12)}$, heterocycloalkyloxy$_{(C\leq12)}$, heteroaryloxy$_{(C\leq12)}$, alkylamino$_{(C\leq12)}$, dialkylamino$_{(C\leq12)}$, arylamino$_{(C\leq12)}$, aralkylamino$_{(C\leq12)}$, or a substituted version of any of these groups; n is 0, 1, 2, 3, 4, or 5; $R_2$ is hydrogen, or alkyl$_{(C\leq12)}$, cycloalkyl$_{(C\leq12)}$, alkenyl$_{(C\leq12)}$, cycloalkenyl$_{(C\leq12)}$, aryl$_{(C\leq12)}$, acyl$_{(C\leq12)}$, or a substituted version of any of these groups; $R_3$ and $R_4$ are each independently selected from hydrogen, halo, hydroxy, amino, or alkyl$_{(C\leq12)}$, cycloalkyl$_{(C\leq12)}$, alkenyl$_{(C\leq12)}$, cycloalkenyl$_{(C\leq12)}$, aryl$_{(C\leq12)}$, aralkyl$_{(C\leq12)}$, heterocycloalkyl$_{(C\leq12)}$, acyl$_{(C\leq12)}$, alkoxy$_{(C\leq12)}$, cycloalkoxy$_{(C\leq12)}$, amido$_{(C\leq12)}$ or a substituted version of any of these groups; and $X_1$ and $X_2$ are each independently selected from =N— or =CR$_5$— wherein $R_5$ is hydrogen, halo, hydroxy, amino, alkyl$_{(C\leq12)}$, cycloalkyl$_{(C\leq12)}$, aryl$_{(C\leq12)}$, acyl$_{(C\leq12)}$, alkoxy$_{(C\leq12)}$, amido$_{(C\leq12)}$, substituted alkyl$_{(C\leq12)}$, substituted cycloalkyl$_{(C\leq12)}$, substituted aryl$_{(C\leq12)}$, substituted-acyl$_{(C\leq12)}$, substituted alkoxy$_{(C\leq12)}$, or substituted-amido$_{(C\leq12)}$; comprising reacting a compound of the formula:

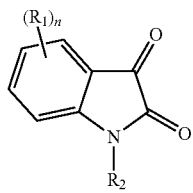

(V)

wherein: $R_1$ is hydrogen, hydroxy, halo, amino, carboxy, nitro, cyano, phosphate, sulfate, or alkyl$_{(C\leq12)}$, cycloalkyl$_{(C\leq12)}$, alkenyl$_{(C\leq12)}$, cycloalkenyl$_{(C\leq12)}$, alkynyl$_{(C\leq12)}$, aryl$_{(C\leq12)}$, aralkyl$_{(C\leq12)}$, heterocycloalkyl$_{(C\leq12)}$, heteroaryl$_{(C\leq12)}$, acyl$_{(C\leq12)}$, amido$_{(C\leq12)}$, alkoxy$_{(C\leq12)}$, cycloalkoxy$_{(C\leq12)}$, aryloxy$_{(C\leq12)}$, aralkyloxy$_{(C\leq12)}$, heterocycloalkyloxy$_{(C\leq12)}$, heteroaryloxy$_{(C\leq12)}$, alkylamino$_{(C\leq12)}$, dialkylamino$_{(C\leq12)}$, arylamino$_{(C\leq12)}$, aralkylamino$_{(C\leq12)}$, or a substituted version of any of these groups; n is 0, 1, 2, 3, 4, or 5; $R_2$ is hydrogen, or alkyl$_{(C\leq12)}$, cycloalkyl$_{(C\leq12)}$, alkenyl$_{(C\leq12)}$, cycloalkenyl$_{(C\leq12)}$, aryl$_{(C\leq12)}$, acyl$_{(C\leq12)}$, or a substituted version of any of these groups; in a reaction with a compound of the formula:

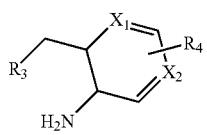

(VI)

wherein: $R_3$ and $R_4$ are each independently selected from hydrogen, halo, hydroxy, amino, or alkyl$_{(C\leq12)}$, cycloalkyl$_{(C\leq12)}$, alkenyl$_{(C\leq12)}$, cycloalkenyl$_{(C\leq12)}$, aryl$_{(C\leq12)}$, aralkyl$_{(C\leq12)}$, heterocycloalkyl$_{(C\leq12)}$, acyl$_{(C\leq12)}$, alkoxy$_{(C\leq12)}$, cycloalkoxy$_{(C\leq12)}$, amido$_{(C\leq12)}$ or a substituted version of any of these groups; and $X_1$ and $X_2$ are each independently selected from =N— or =CR$_5$— wherein $R_5$ is hydrogen, halo, hydroxy, amino, alkyl$_{(C\leq12)}$, cycloalkyl$_{(C\leq12)}$, aryl$_{(C\leq12)}$, acyl$_{(C\leq12)}$, alkoxy$_{(C\leq12)}$, amido$_{(C\leq12)}$, substituted alkyl$_{(C\leq12)}$, substituted cycloalkyl$_{(C\leq12)}$, substituted aryl$_{(C\leq12)}$, substituted acyl$_{(C\leq12)}$, substituted alkoxy$_{(C\leq12)}$, or substituted amido$_{(C\leq12)}$; in the presence of an acid and under microwave irradiation. In some embodiments, the compound of formula V is further defined as:

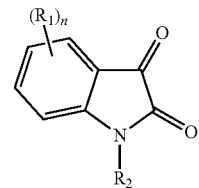

(V)

wherein: $R_1$ is hydrogen, hydroxy, halo, amino, carboxy, nitro, cyano, phosphate, sulfate, or alkyl$_{(C\leq12)}$, cycloalkyl$_{(C\leq12)}$, alkoxy$_{(C\leq12)}$, cycloalkoxy$_{(C\leq12)}$, alkylamino$_{(C\leq12)}$, dialkylamino$_{(C\leq12)}$, or a substituted version of any of these groups; n is 0, 1, 2, or 3; and $R_2$ is hydrogen, or alkyl$_{(C\leq12)}$, cycloalkyl$_{(C\leq12)}$, alkenyl$_{(C\leq12)}$, cycloalkenyl$_{(C\leq12)}$, aryl$_{(C\leq12)}$, acyl$_{(C\leq12)}$, or a substituted version of any of these groups. In some embodiments, the compound of formula VI is further defined as:

(VI)

wherein: $R_3$ and $R_4$ are each independently selected from hydrogen, halo, hydroxy, amino, or alkyl$_{(C\leq12)}$, cycloalkyl$_{(C\leq12)}$, alkoxy$_{(C\leq12)}$, cycloalkoxy$_{(C\leq12)}$, or a substituted version of any of these groups; and $X_1$ and $X_2$ are each independently selected from =N— or =CR$_5$— wherein $R_5$ is hydrogen, halo, hydroxy, amino, alkyl$_{(C\leq12)}$, cycloalkyl$_{(C\leq12)}$, alkoxy$_{(C\leq12)}$, substituted alkyl$_{(C\leq12)}$, substituted cycloalkyl$_{(C\leq12)}$, or substituted alkoxy$_{(C\leq12)}$. In some embodiments, the compound of formula IV is further defined as:

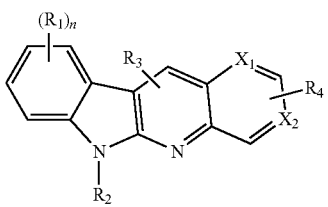

(IV)

wherein: $R_1$ is hydrogen, hydroxy, halo, amino, carboxy, nitro, cyano, phosphate, sulfate, or alkyl$_{(C\leq12)}$, cycloalkyl$_{(C≤12)}$, alkoxy$_{(C≤12)}$, cycloalkoxy$_{(C≤12)}$, alkylamino$_{(C≤12)}$, dialkylamino$_{(C≤12)}$, or a substituted version of any of these groups; n is 0, 1, 2, or 3; $R_2$ is hydrogen, or alkyl$_{(C≤12)}$, cycloalkyl$_{(C≤12)}$, alkenyl$_{(C≤12)}$, cycloalkenyl$_{(C≤12)}$, aryl$_{(C≤12)}$, acyl$_{(C≤12)}$, or a substituted version of any of these groups; $R_3$ and $R_4$ are each independently selected from hydrogen, halo, hydroxy, amino, or alkyl$_{(C≤12)}$, cycloalkyl$_{(C≤12)}$, alkoxy$_{(C≤12)}$, cycloalkoxy$_{(C≤12)}$, or a substituted version of any of these groups; and $X_1$ and $X_2$ are each independently selected from =N— or =CR$_5$— wherein $R_5$ is hydrogen, halo, hydroxy, amino, alkyl$_{(C≤12)}$, cycloalkyl$_{(C≤12)}$, alkoxy$_{(C≤12)}$, substituted alkyl$_{(C≤12)}$, substituted cycloalkyl$_{(C≤12)}$, or substituted alkoxy$_{(C≤12)}$. In some embodiments, the method further comprises a solvent. In some embodiments, the solvent is an organic solvent. In some embodiments, the solvent is water. In some embodiments, the method comprises adding from about 1.5 to about 5 equivalents of the compound of formula VI relative to the compound of formula V. In some embodiments, the method comprises adding about 3.0 equivalents of the compound of formula VI relative to the compound of formula V. In some embodiments, the method comprises adding from about 0.01 equivalents to about 3.0 equivalent of acid to the reaction relative to the compound of formula V. In some embodiments, the method comprises adding 0.2 equivalents of acid to the reaction relative to the compound of formula V. In some embodiments, the acid is trifluoroacetic acid, hydrochloric acid, hydrobromic acid, hydroiodic acid, sulfuric acid, boron trifluoride etherate, or trifluoromethanesulfonic acid. In some embodiments, the acid is hydrochloric acid, trifluoroacetic acid, or trifluoromethanesulfonic acid. In some embodiments, the reaction further comprises heating to a temperature from about 100° C. to about 225° C. In some embodiments, the temperature is about 150° C. In some embodiments, the method further comprises reacting the compound of formula IV with the compound of formula V for a time period from about 3 hours to about 48 hours. In some embodiments, the time period is from about 3 hours to about 24 hours. In some embodiments, the time period is from about 6 hours to about 18 hours. In some embodiments, the time period is about 12 hours. In some embodiments, the method further comprises purifying the reaction after the time period. In some embodiments, the purification is chromatography. In some embodiments, the chromatography is C18 reverse phase chromatography.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

DETAILED DESCRIPTION

Disclosed herein are new methods of preparation, compounds, methods of treatment, and compositions of aza-ellipticine. Using a novel microwave based synthetic method with a picoline and an isatin compound, novel aza-ellipticine were developed which may be useful in treating cancer (Stiborova, et al., 2012), HIV (Mathe, et al., 1998), malaria (Pohlit, et al., 2012), or other diseases. This novel synthetic method also provides a route to easily access a host of new and potentially useful aza-ellipticine analogs.

I. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; "sulfate" means —S(O)$_2$OH; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⩵" represents a single bond or a double bond. Thus, for example, the formula

includes

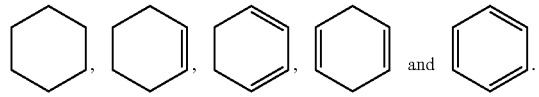

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "〜〜", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◂▬" means a single bond where the group attached to the thick end of the wedge is "out of the page." The symbol "⦀⦀⦀" means a single bond where the group attached to the thick end of the wedge is "into the page". The symbol "〜〜" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom.

When a group "R" is depicted as a "floating group" on a ring system, for example, in the formula:

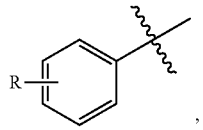

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

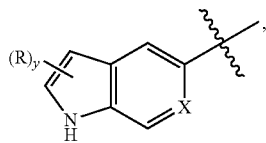

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C\leq 8)}$" or the class "alkene$_{(C\leq 8)}$," is two. For example, "alkoxy$_{(C\leq 10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, and —CH$_2$CH$_2$CH$_2$—, are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, a linear or branched cyclo or cyclic structure, no carbon-carbon double or triple bonds, and no atoms other than carbon and hydrogen. As used herein, the cycloalkyl group may contain one or more branching alkyl groups (carbon number limit permitting) attached to the ring system so long as the point of attachment is the ring system. Non-limiting examples of cycloalkyl groups include: —CH(CH$_2$)$_2$ (cyclopropyl), cyclobutyl, cyclopentyl, or cyclohexyl. The term "cycloalkanediyl" when used without the "substituted" modifier refers to a divalent saturated aliphatic group with one or two carbon atom as the point(s) of attachment, a linear or branched cyclo or cyclic structure, no carbon-carbon double or triple bonds, and no atoms other than carbon and hydrogen.

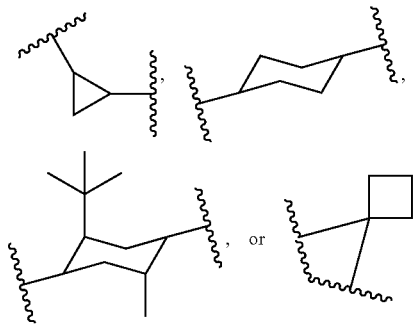

are non-limiting examples of cycloalkanediyl groups. The term "cycloalkylidene" when used without the "substituted" modifier refers to the divalent group =CRR' in which R and R' are taken together to form a cycloalkanediyl group with at least two carbons. Non-limiting examples of alkylidene groups include: =C(CH$_2$)$_2$ and =C(CH$_2$)$_5$. A "cycloalkane" refers to the compound H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted cycloalkyl groups: —C(OH)(CH$_2$)$_2$,

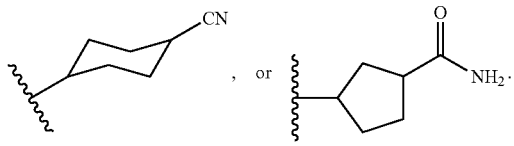 [SMILES: *C1CCC(C#N)CC1 ; *C1CCC(C(N)=O)C1]

The term "alkenyl" when used without the "substituted" modifier refers to a monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

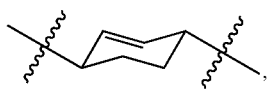 [SMILES: *C1C=CC(*)CC1]

are non-limiting examples of alkenediyl groups. It is noted that while the alkenediyl group is aliphatic, once connected at both ends, this group is not precluded from forming part of an aromatic structure. The terms "alkene" and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups.

The term "cycloalkenyl" when used without the "substituted" modifier refers to a monovalent unsaturated aliphatic group with a carbon atom as the point of attachment, a linear or branched cyclo or cyclic structure, at least one non-aromatic carbon-carbon double bond, no carbon-carbon triple bonds, and no atoms other than carbon and hydrogen. As used herein, the cycloalkenyl group may contain one or more branching alkyl groups (carbon number limit permitting) attached to the ring system so long as the point of attachment is the ring system. In some non-limiting examples of cycloalkenyl groups include

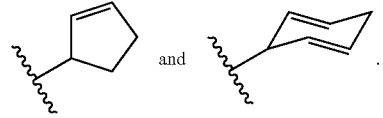 [SMILES: *C1C=CCC1 ; *C1C=CCC=C1]

The term "cycloalkenediyl" when used without the "substituted" modifier refers to a divalent unsaturated aliphatic group with one or two carbon atom(s) as the point(s) of attachment, a linear or branched cyclo or cyclic structure, at least one non-aromatic carbon-carbon double bond, no carbon-carbon triple bonds, and no atoms other than carbon and hydrogen.

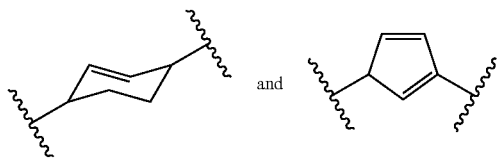 [SMILES: *C1C=CC(*)CC1 ; *C1=CC(*)C=C1]

are non-limiting examples of cycloalkenediyl. It is noted that while the cycloalkenediyl group is aliphatic, once connected at both ends, this group is not precluded from forming part of an aromatic structure. The terms "cycloalkene" and refer to a compound having the formula H—R, wherein R is cycloalkenyl as this term is defined above. The term "olefin" is synonymous with the terms "alkene" or a "cycloalkane" as those terms are defined above. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. In some non-limiting examples of substituted cycloalkenyl include

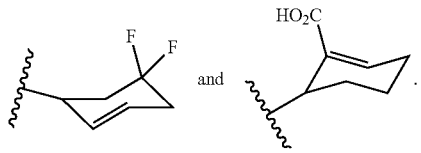 [SMILES: *C1C=CCC(F)(F)C1 ; *C1CCCC=C1C(=O)O]

The term "alkynyl" when used without the "substituted" modifier refers to a monovalent unsaturated aliphatic group with a carbon atom as the point of attachment, a linear or branched, acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

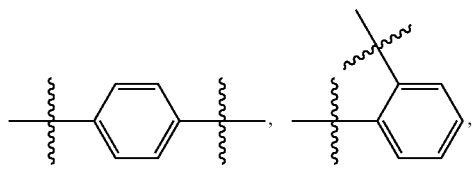

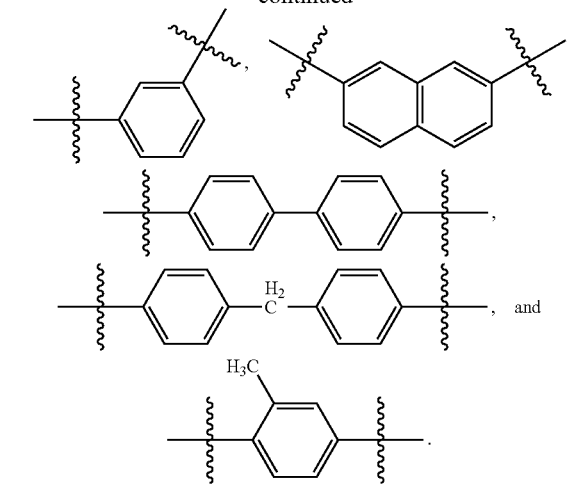

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

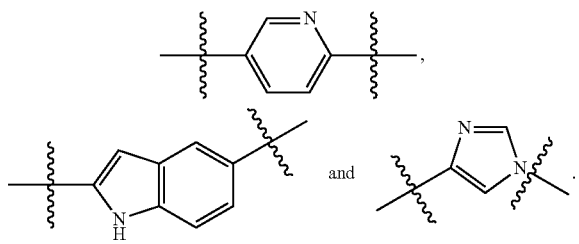

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "heteroaralkyl" when used without the "substituted" modifier refers to the monovalent group -alkanediyl-heteroaryl, in which the terms alkanediyl and heteroaryl are each used in a manner consistent with the definitions provided above. Non-limiting examples of heteroaralkyls are: 2-pyridylmethyl and 2-indazolyl-ethyl. When the term heteroaralkyl is used with the "substituted" modifier one or more hydrogen atom from the alkanediyl and/or the heteroaryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted heteroaralkyls are: (3-chloroquinolyl)-methyl, and 2-chloro-2-thienyl-eth-1-yl.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. The term "heterocycloalkanediyl" when used without the "substituted" modifier refers to an divalent cyclic group, with two carbon atoms, two nitrogen atoms, or one carbon atom and one nitrogen atom as the two points of attachment, said atoms forming part of one or more ring structure(s) wherein at least one of the ring atoms is nitrogen, oxygen or sulfur, and wherein the divalent group consists of no atoms other than carbon, hydrogen, nitrogen, oxygen and sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkanediyl groups include:

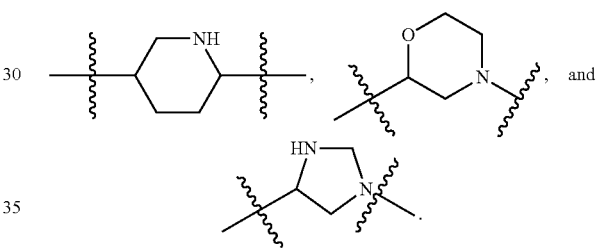

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$NH$_2$, or —C(O)OC(CH$_3$)$_3$ (tert-butyloxycarbonyl, BOC).

The term "acyl" when used without the "substituted" modifier refers to the group —C(O)R, in which R is a hydrogen, alkyl, cycloalkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO₂CH₃ (methylcarboxyl), —CO₂CH₂CH₃, —C(O)NH₂ (carbamoyl), and —CON(CH₃)₂, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH₃ (methoxy), —OCH₂CH₃ (ethoxy), —OCH₂CH₂CH₃, —OCH(CH₃)₂ (isopropoxy), and —OC(CH₃)₃ (tert-butoxy). The terms "cycloalkoxy", "alkenyloxy", "cycloalkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, cycloalkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The terms "alkylthio", "cycloalkylthio", and "acylthio" when used without the "substituted" modifier refers to the group —SR, in which R is an alkyl, cycloalkyl, and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy or cycloalkoxy group. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂.

The term "alkylamino" when used without the "substituted" modifier refers to the group —NHR, in which R is an alkyl, as that term is defined above. Non-limiting examples of alkylamino groups include: —NHCH₃ and —NHCH₂CH₃. The term "dialkylamino" when used without the "substituted" modifier refers to the group —NRR', in which R and R' can each independently be the same or different alkyl groups, or R and R' can be taken together to represent an alkanediyl. Non-limiting examples of dialkylamino groups include: —N(CH₃)₂, —N(CH₃)(CH₂CH₃), and N-pyrrolidinyl. The terms "alkoxyamino", "cycloalkylamino", "alkenylamino", "cycloalkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, cycloalkyl, alkenyl, cycloalkenyl, alkynyl, aryl, aralkyl, heteroaryl, heterocycloalkyl, and alkylsulfonyl, respectively. A non-limiting example of an arylamino group is —NHC₆H₅. The term "amido" (acylamino), when used without the "substituted" modifier, refers to the group —NHR, in which R is acyl, as that term is defined above. A non-limiting example of an amido group is —NHC(O)CH₃. The term "alkylimino" when used without the "substituted" modifier refers to the divalent group =NR, in which R is an alkyl, as that term is defined above. The term "alkyliminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. The groups —NHC(O)OCH₃ and —NHC(O)NHCH₃ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "IC₅₀" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methane-sulfonates, ethanesulfonates, benzenesulfonates, p-toluenesulfonates, cyclohexyl-sulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

Other abbreviations used herein are as follows: $^1$H NMR, proton nuclear magnetic resonance spectroscopy; DMSO, dimethyl sulfoxide; h or hr, hour(s); rt, retention time; NOE, nuclear overhauser effect; and COSY, correlation spectroscopy.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. Compounds and Synthetic Methods

The compounds provided by the present disclosure are shown here and above in the summary of the invention section and in the claims below. For example, the compounds could be of the formula:

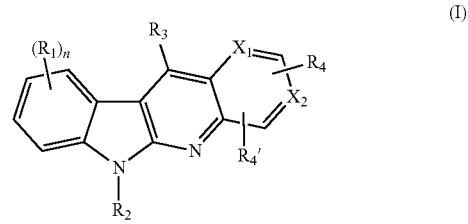

(I)

wherein: $R_1$ is hydrogen, hydroxy, halo, amino, carboxy, nitro, cyano, phosphate, sulfate, or alkyl$_{(C \leq 12)}$, cycloalkyl$_{(C \leq 12)}$, alkenyl$_{(C \leq 12)}$, cycloalkenyl$_{(C \leq 12)}$, alkynyl$_{(C \leq 12)}$, aryl$_{(C \leq 12)}$, aralkyl$_{(C \leq 12)}$, heterocycloalkyl$_{(C \leq 12)}$, heteroaryl$_{(C \leq 12)}$, acyl$_{(C \leq 12)}$, amido$_{(C \leq 12)}$, alkoxy$_{(C \leq 12)}$, cycloalkoxy$_{(C \leq 12)}$, aryloxy$_{(C \leq 12)}$, aralkyloxy$_{(C \leq 12)}$, heterocycloalkyloxy$_{(C \leq 12)}$, heteroaryloxy$_{(C \leq 12)}$, alkylamino$_{(C \leq 12)}$, dialkylamino$_{(C \leq 12)}$, arylamino$_{(C \leq 12)}$, aralkylamino$_{(C \leq 12)}$, or a substituted version of any of these groups; n is 0, 1, 2, 3, 4, or 5; $R_2$ is hydrogen, or alkyl$_{(C \leq 12)}$, cycloalkyl$_{(C \leq 12)}$, alkenyl$_{(C \leq 12)}$, cycloalkenyl$_{(C \leq 12)}$, aryl$_{(C \leq 12)}$, acyl$_{(C \leq 12)}$, or a substituted version of any of these groups; $R_3$, $R_4$, and $R_4'$ are each independently selected from hydrogen, halo, hydroxy, amino, or alkyl$_{(C \leq 12)}$, cycloalkyl$_{(C \leq 12)}$, alkenyl$_{(C \leq 12)}$, cycloalkenyl$_{(C \leq 12)}$, aryl$_{(C \leq 12)}$, aralkyl$_{(C \leq 12)}$, heterocycloalkyl$_{(C \leq 12)}$, acyl$_{(C \leq 12)}$, alkoxy$_{(C \leq 12)}$, cycloalkoxy$_{(C \leq 12)}$, amido$_{(C \leq 12)}$ or a substituted version of any of these groups; and $X_1$ and $X_2$ are each independently selected from =N— or =CR$_5$— wherein $R_5$ is hydrogen, halo, hydroxy, amino, alkyl$_{(C \leq 12)}$, cycloalkyl$_{(C \leq 12)}$, aryl$_{(C \leq 12)}$, acyl$_{(C \leq 12)}$, alkoxy$_{(C \leq 12)}$, amido$_{(C \leq 12)}$, substituted alkyl$_{(C \leq 12)}$, substituted cycloalkyl$_{(C \leq 12)}$, substituted aryl$_{(C \leq 12)}$, substituted acyl$_{(C \leq 12)}$, substituted alkoxy$_{(C \leq 12)}$, or substituted amido$_{(C \leq 12)}$; or a pharmaceutically acceptable salt or tautomer thereof.

They may be made using the methods outlined in the Examples section. The compounds provided by the present disclosure are shown, for example, above in the summary of the invention section and in the claims below. They may be made using the methods outlined in the Examples section. These methods can be further modified using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds of the invention may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

Those skilled in the art of organic chemistry will appreciate that many organic compounds can form complexes with solvents in which they are reacted or from which they are precipitated or crystallized. These complexes are known as "solvates." For example, a complex with water is known as a "hydrate." Solvates of the compounds provided herein are within the scope of the invention. It will also be appreciated by those skilled in organic chemistry that many organic compounds can exist in more than one crystalline form. For example, crystalline form may vary from solvate to solvate. Thus, all crystalline forms of the compounds provided herein or the pharmaceutically acceptable solvates thereof are within the scope of the present invention.

It should be further recognized that the compounds of the present invention include those that have been further modified to comprise substituents that are convertible to hydrogen in vivo. This includes those groups that may be convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydropyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl (—C(O)OC(CH$_3$)$_3$, Boc), benzyloxycarbonyl, p-methoxy-benzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$, Boc), and the like. Suitable peptide residues include peptide residues comprising two to five amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and haloethoxycarbonyl groups (such as β,β,β-trichloroethoxycarbonyl and β-iodoethoxycarbonyl).

Compounds of the invention may also have the advantage that they may be more efficacious than, be less toxic than, be longer acting than, be more potent than, produce fewer side effects than, be more easily absorbed than, have a better pharmacokinetic profile (e.g., higher oral bioavailability and/or lower clearance) and/or be easier to produce on industrial useful scales than, and/or have other useful pharmacological, physical, or chemical properties over, compounds known in the prior art, whether for use in the indications stated herein or otherwise.

III. Pharmaceutical Formulations and Routes of Administration

The compounds of the present disclosure may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include: sterile aqueous solutions (where water soluble), dispersions, and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. For example, the efficacy of a compound can be evaluated in an animal model system that may be predictive of efficacy in treating the disease in humans, such as the model systems shown in the examples and drawings.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milli-gram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the subject has eaten or will eat.

IV. Combination Therapy

In addition to being used as a monotherapy, the compounds of the present invention may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Non-limiting examples of such combination therapy include combination of one or more compounds of the invention with another chemotherapeutic agent, surgery radiation therapy, an immunotherapy, or an anti-infective agent. Compounds of the invention may be combined with agents designed to improve a patient's immune response to cancer, including (but not limited to) cancer vaccines.

EXAMPLES

The following examples are included to demonstrate representative embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

I. Preparation of Representative Intermediates 2-pentylpyridin-3-amine

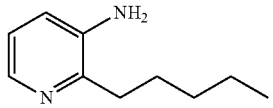

To an oven dried Biotage microwave vial equipped with a stir bar, cooled under argon, was added 2-bromo-3-aminoprydine (0.258 grams, 1.5 mmol), Cs2CO3 (0.731 grams, 2.25 mmol), and Pd(PPH3)4 (0.105 grams, 0.1 mmol). The mixture was taken up in 4.0 mL THF and 1.0 mL water. (E)-4,4,5,5-tetramethyl-2-(pent-1-en-1-yl)-1,3,2-dioxaborolane (0.43 mL, 1.95 mmol) was then added. The mixture was sparged with argon for 20 minutes. The solution was sealed, placed in the Biotage microwave Initiator and heated at 120° C. for 3 hours. The solution was then salted out, and the organic material extracted using ethyl acetate. The aqueous material was washed twice with ethyl acetate. The combined organic material was dried with Na2SO4, filtered, and concentrated. It was then used for the next step without further purification.

To a Parr Bomb flask charged with crude material was added 20.0 mL of methanol followed by 0.05 grams of Pd/C (10%). The flask was then placed in a Parr Bomb apparatus where the reaction was carefully submitted to a hydrogen atmosphere at 55 psi. The mixture was oscillated at this pressure over night. The next day, the reaction was filtered through a plug of celite. The plug was then rinsed with several washing of methanol. The solution was then concentrated. The product from this reaction was used without any further purification.

2-ethylpyridin-3-amine

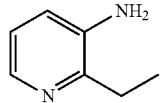

Was made in the manner described by ⊠ Heidelbaugh, Todd M.; Cappiello, John R.; Nguyen, Phong; Gomez, Dario G. PCT Int. Appl. (2011), WO 2011050054 A2 20110428.

5-methoxy-1-propylindoline-2,3-dione

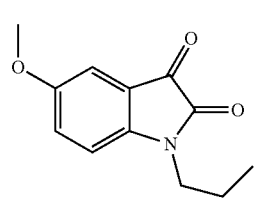 [SMILES: CCCN1C(=O)C(=O)c2cc(OC)ccc21]

To an oven dried Biotage microwave vial equipped with a stir bar, cooled under argon, was added 5-methoxy-isatin (0.709 grams, 4.0 mmol) K2CO3, (0.829 grams, 6.0 mmol) and potassium iodide (0.0664 grams, 0.4 mmol). The mixture was taken up in 18.0 mL of anhydrous DMF. While stirring at room temperature 1-bromopropane (0.45 mL, 4.8 mmol) was added. The vial was then sealed, placed in the Biotage microwave Initiator and heated on a setting of low to 100° C. for 1 hour. The DMF was then removed using a rotovap. The residue was taken up in ethyl acetate and celite, and filtered. The celite plug was rinsed with ethyl acetate until no more color eluted. The organic solution was then concentrated. Purification done using a Teledyne ISCO Combiflash on a silica support using hexanes: ethyl acetate gradient. Collected 0.835 grams. Yield, 95% MS Chemical Formula: $C_{12}H_{13}NO_3$ calculated mass 219.09, observed 220.1 (m+1).

1-propylindoline-2,3-dione

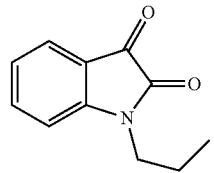

Made in a similar way to 5-methoxy-1-propylindoline-2,3-dione.

5-methyl-1-propylindoline-2,3-dione

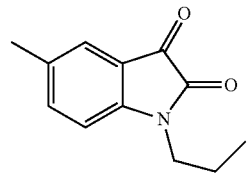

Was made in a similar way to 5-methoxy-1-propylindoline-2,3-dione.

5-chloro-1-propylindoline-2,3-dione

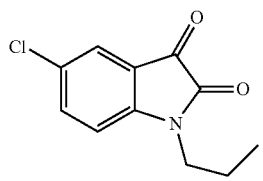

Was made in a similar way to 5-methoxy-1-propylindoline-2,3-dione.

5-hydroxyindoline-2,3-dione

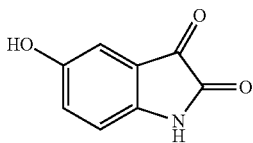 [SMILES: O=C1Nc2ccc(O)cc2C1=O]

Was made in the manner described by Yasuda, Daisuke; Takahashi, Kyoko; Ohe, Tomoyuki; Nakamura, Shigeo; Mashino, Tadahiko Bioorganic & Medicinal Chemistry (2013), 21(24), 7709-7714.

II. Preparation of Representative Embodiments

Preparative Example A

Novel aza-ellipticine compounds were prepared using a protic acid in an organic solvent in the presence of microwave irradiation and heating resulted in a mixture of aza-ellipticines and imine cores. Reaction conditions are described in Table 1. Acid concentration and time were first explored as methods to reduce the formation of the imine product. The greatest increases in yield were obtained when moving to a polar solvent system. Various strength acids as well as Lewis acids were used and trifluoromethanesulfonic acid (TfOH) was selected as TfOH required only sub-stoichiometric amounts of acid without reducing the reaction time. Reasonable conversion was also seen with hydrochloric acid.

TABLE 1

Reaction Conditions

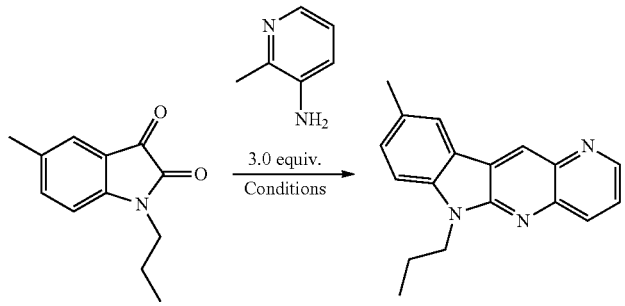

| Entry | Acid (equiv.) | Solvent (Concentration) | Temperature | Time |
|---|---|---|---|---|
| A | TFA (0.3 equiv.) | 1,4 dioxane (0.3 M) | 110° C. | 48 hrs |
| B | TFA (2.0 equiv.), | Dioxane/H$_2$O (3:1 @ 0.1 M) | 130° C. | 18 hr |
| C | TfOH (0.2 equiv.) | EtOH (0.1 M) | 150° C. | 1 hr |
| D | TfOH (0.2 equiv.) | Dioxane/H$_2$O (3:1 @ 0.1 M) | 130° C. | 1 hr |
| E | TfOH (0.2 equiv.) | Dioxane/H$_2$O (1:1 @ 0.1 M) | 130° C. | 1 hr |
| F | TfOH (0.2 equiv.) | H$_2$O (0.2 M) | 150° C. | 12 hr |
| G | BF$_3$Et$_2$O (0.2 equiv.), | toluene (0.1 M) | 120° C. | 48 hrs |
| H | BF$_3$Et$_2$O (0.2 equiv.), | CH$_2$Cl$_2$ (0.1 M) | RT | 48 hrs |
| I | HCl (0.2 equiv.) | H$_2$O (0.2 M) | 150° C. | 12 hrs |

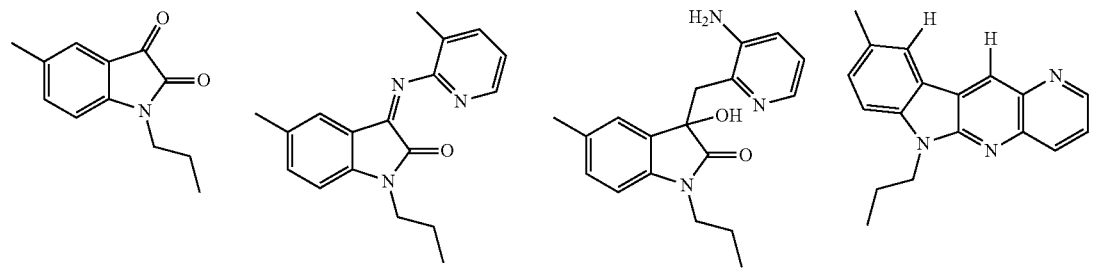

| Entry | | relative product ratio[i] | | |
|---|---|---|---|---|
| A | 8 | 71 | 0.1 | 19 |
| B | 28 | 0.2 | 0.5 | 71 |
| C | 20 | 27 | 2 | 1 |
| D | 73 | 9 | 17 | 1 |
| E | 78 | 15 | 15 | 1 |
| F | 0 | 0 | 0 | 91 |
| G | 10 | 39 | — | 1 |
| H | 2 | 1 | — | — |
| I | 47 | 3 | 3 | 47 |

Preparative Example B

The aza-ellipticine analogs were produced using the following general reaction method. To a clean microwave safe reaction vial equipped with a stir bar was added the appropriate isatin analog (1.0 equiv., 0.2M in H$_2$O) and aminopicoline (3.0 equiv.). A concentrated acid like trifluoromethanesulfonic acid, or concentrated hydrochloric acid (0.2 equiv.) was then added. The vial was sealed and heated in a microwave at 150° C. for 12 hours. The solvent was then removed using a rotary evaporator and the residue purified on a Teledyne ISCO chromatography system using a C18 reverse phase support (H$_2$O with 0.1% Formic acid/MeCN gradient) to afford the desired aza-ellipticine analog. A summary of the compounds synthesized can be found in Table 2.

TABLE 2

Compounds Produced by Microwave Irradiation

| Example | Isatin | Picoline | Product | Yield |
|---|---|---|---|---|
| 1 | (isatin) | 2-methyl-3-aminopyridine | aza-ellipticine analog | 40% |
| 2 | (isatin) | 4-methyl-3-aminopyridine | aza-ellipticine analog | 53% |
| 3 | (N-propyl isatin) | 2-methyl-3-aminopyridine | aza-ellipticine analog | 60% |
| 4 | (N-propyl isatin) | 4-methyl-3-aminopyridine | aza-ellipticine analog | 78% |
| 5 | (5-methyl-N-propyl isatin) | 2-methyl-3-aminopyridine | aza-ellipticine analog | 61% |

TABLE 2-continued
Compounds Produced by Microwave Irradiation
| Example | Isatin | Picoline | Product | Yield |
|---|---|---|---|---|
| 6 | 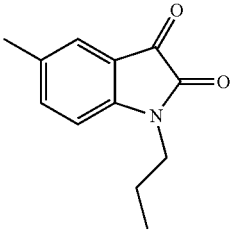 | 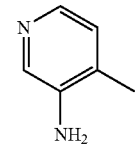 | 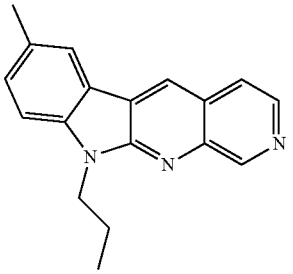 [SMILES: CCCn1c2ccc(C)cc2c2cc3ccncc3nc21] | 40% |
| 7 | 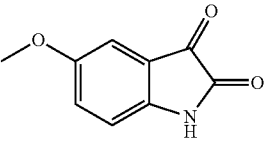 | 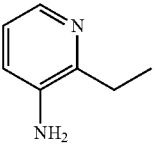 | 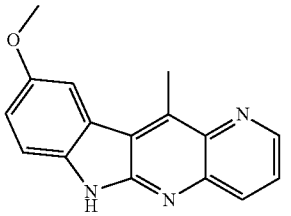 [SMILES: COc1ccc2[nH]c3nc4cccnc4c(C)c3c2c1] | 20% |
| 8 | 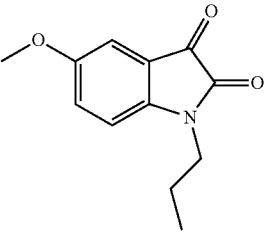 [SMILES: CCCN1C(=O)C(=O)c2cc(OC)ccc21] | 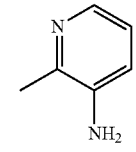 | 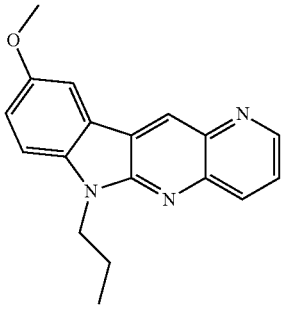 [SMILES: CCCn1c2ccc(OC)cc2c2cc3ncccc3nc21] | 55% |
| 9 | 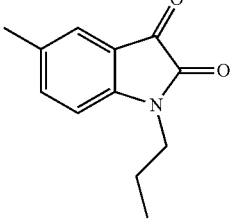 | 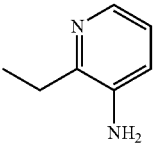 | 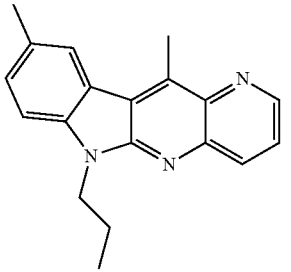 [SMILES: CCCn1c2ccc(C)cc2c2c(C)c3ncccc3nc21] | 30% |
| 10 | 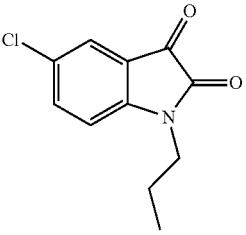 | 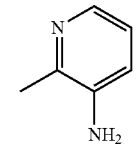 | 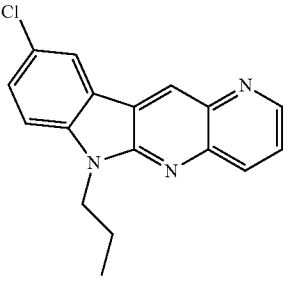 [SMILES: CCCn1c2ccc(Cl)cc2c2cc3ncccc3nc21] | 60% |

TABLE 2-continued

Compounds Produced by Microwave Irradiation

| Example | Isatin | Picoline | Product | Yield |
|---|---|---|---|---|
| 11 | 5-chloro-1-propyl isatin | 3-amino-4-methylpyridine | 9-chloro-7-propyl pyrido-indole derivative | 70% |
| 12 | 5-methoxy isatin | 3-amino-2-methylpyridine | methoxy pyrido-indole derivative | 18% |
| 13 | 5-methoxy isatin | 3-amino-4-methylpyridine | methoxy pyrido-indole derivative | 10% |
| 14 | 5-hydroxy isatin | 3-amino-2-methylpyridine | hydroxy pyrido-indole derivative | 15% |
| 15 | 7-methoxy isatin | 3-amino-2-methylpyridine | methoxy pyrido-indole derivative | 20% |
| 16 | 5-methoxy-1-propyl isatin | 3-amino-4-methylpyridine | methoxy-propyl pyrido-indole derivative | 23% |

TABLE 2-continued

Compounds Produced by Microwave Irradiation

| Example | Isatin | Picoline | Product | Yield |
|---|---|---|---|---|
| 17 | | | | 12% |
| 18 | | | | 30% |
| 19 | | | | 10% over two steps |
| 20 | | | | 20% |

Example 1

6H-indolo[2,3-b][1,5]naphthyridine

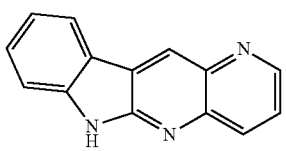 [SMILES: c1cnc2cc3c(nc2c1)[nH]c1ccccc13]

The compound was synthesized as shown in Preparative Example B above. Purification done using a Teledyne ISCO Combiflash on a silica support using Dichloromethane:Acetonitrile (9:1). HPLC run on Agilent 1100 using water w/0.1% Formic acid:Acetonitrile 95:5 to 100% MeCN over a ten minute gradient on phenomenex 75×4.6 mm C18 column. Rt: 4.8 minutes. $^1$H-NMR (400 MHz, CD3OD) d 9.01 (s, 1H), 8.87 (dd, 1H), 8.45 (d, 1H), 8.30 (d, 1H), 7.77 (dd, 1H), 7.58 (m, 2H), 7.35 (dd, 1H). MS Chemical Formula: $C_{14}H_9N_3$, calculated mass, 219.08, observed 220.1 (M+1).

Example 2

10H-indolo[2,3-b][1,7]naphthyridine

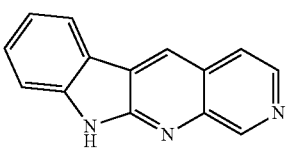 [SMILES: c1ccc2c(c1)[nH]c1nc3cnccc3cc12]

The compound was synthesized as shown in Preparative Example B above. Purification done using a Teledyne ISCO Combiflash on a silica support using hexanes: isopropanol gradient. HPLC run on Agilent 1100 using water w/0.1% Formic acid:Acetonitrile 95:5 to 100% MeCN over a ten minute gradient on phenomenex 75×4.6 mm C18 column. Rt: 4.1 minutes. $^1$H-NMR (400 MHz, CD3OD) d 9.34 (s, 1H), 9.01 (s, 1H), 8.44 (d, 1H), 8.30 (d, 1H), 8.05 (d, 1H), 7.63 (dd, 1H), 7.57 (d, 1H), 7.35 (dd, 1H). MS Chemical Formula: $C_{14}H_9N_3$, calculated mass, 219.08, observed 220.1 (M+1).

Example 3

6-propyl-6H-indolo[2,3-b][1,5]naphthyridine

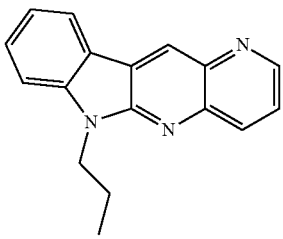 [SMILES: CCCn1c2ccccc2c2cc3ncccc3nc21]

The compound was synthesized as shown in Preparative Example B above. Purification done using a Teledyne ISCO Combiflash on a silica support using hexanes: ethyl acetate gradient. HPLC run on Agilent 1100 using water w/0.1% Formic acid:Acetonitrile 95:5 to 100% MeCN over a ten minute gradient on phenomenex 75×4.6 mm C18 column. Rt: 7.7 minutes. $^1$H-NMR (400 MHz, CDCl3) δ 8.93 (m, 2H), 8.42 (d, 1H), 8.23 (d, 1H), 7.62 (m, 2H), 7.45 (d, 1H), 7.32 (d, 1H), 4.50 (t, 2H), 2.00 (m, 2H), 1.03 (t, 3H). MS Chemical Formula: $C_{17}H_{15}N_3$ calculated mass 261.13, observed 262.2 (m+1).

Example 4

10-propyl-10H-indolo[2,3-b][1,7]naphthyridine

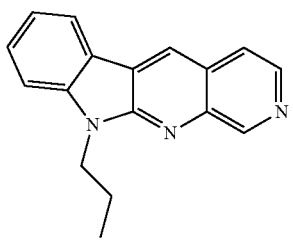 [SMILES: CCCn1c2ccccc2c2cc3ccncc3nc21]

The compound was synthesized as shown in Preparative Example B above. Purification done using a Teledyne ISCO Combiflash on a silica support using hexanes: ethyl acetate gradient. HPLC run on Agilent 1100 using water w/0.1% Formic acid:Acetonitrile 95:5 to 100% MeCN over a ten minute gradient on phenomenex 75×4.6 mm C18 column. Rt: 5.9 minutes. $^1$H-NMR (400 MHz, CDCl3) δ 9.55 (s, 1H), 8.66 (s, 1H), 8.52 (d, 1H), 8.18 (d, 1H), 7.81 (m, 1H), 7.63 (m, 1H), 7.47 (m, 1H), 7.34 (dd, 1H), 4.50 (d, 2H), 2.01 (m, 2H), 1.04 (t, 3H). MS Chemical Formula: $C_{17}H_{15}N_3$ calculated mass 261.13, observed 262.2 (m+1).

Example 5

9=methyl=6=propyl-6H-indolo[2,3-b][1,5]naphthyridine

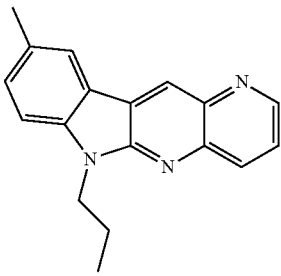 [SMILES: CCCn1c2ccc(C)cc2c2cc3ncccc3nc21]

The compound was synthesized as shown in Preparative Example B above. Purification done using a Teledyne ISCO Combiflash on a silica support using hexanes: ethyl acetate gradient. HPLC run on Agilent 1100 using water w/0.1% Formic acid:Acetonitrile 95:5 to 100% MeCN over a ten minute gradient on phenomenex 75×4.6 mm C18 column. Rt: 8.4 minutes. $^1$H-NMR (400 MHz, CDCl3) δ 8.93 (d, 1H), 8.90 (dd, 1H), 8.43 (d, 1H), 8.04 (d, 1H), 7.63 (m, 1H), 7.44 (m, 1H), 7.36 (d, 1H), 4.48 (t, 2H), 2.58 (s, 3H), 2.00 (m, 2H), 1.03 (t, 3H). MS Chemical Formula: $C_{18}H_{17}N_3$, calculated mass, 275.14, observed 276 (M+1).

Example 6

7-methyl-10-propyl-10H-indolo[2,3-b][1,7]naphthyridine

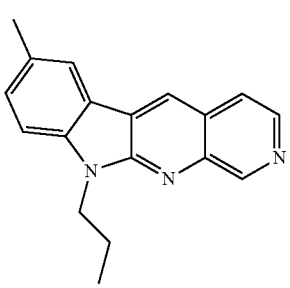 [SMILES: CCCn1c2ccc(C)cc2c2cc3ccncc3nc21]

The compound was synthesized as shown in Preparative Example B above. Purification done using a Teledyne ISCO Combiflash on a silica support using hexanes: ethyl acetate gradient. HPLC run on Agilent 1100 using water w/0.1% Formic acid:Acetonitrile 95:5 to 100% MeCN over a ten minute gradient on phenomenex 75×4.6 mm C18 column. Rt: 6.3 minutes. $^1$H-NMR (400 MHz, CDCl3) δ 9.55 (s, 1H), 8.68 (s, 1H), 8.53 (d, 1H), 8.03 (s, 1H), 7.85 (d, 1H), 7.48 (dd, 1H), 7.39 (d, 1H), 4.52 (t, 2H), 2.58 (s, 3H), 2.0 (m, 2H), 1.03 (t, 3H). MS Chemical Formula: $C_{18}H_{17}N_3$, calculated mass, 275.14, observed 276.1 (m+1).

Example 7

9-methoxy-11-methyl-6H-indolo[2,3-b][1,5]naphthyridine

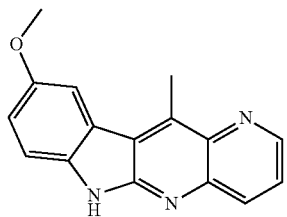 [SMILES: COc1ccc2[nH]c3nc4cccnc4c(C)c3c2c1]

The compound was synthesized as shown in Preparative Example B above. Purification done using a Teledyne ISCO Combiflash on a C18 support using water:acetonitrile gradient. HPLC run on Agilent 1100 using water w/0.1% Formic acid:Acetonitrile 95:5 to 100% MeCN over a ten minute gradient on phenomenex 75×4.6 mm C18 column. Rt: 5.9 minutes. $^1$H-NMR (400 MHz, CD3OD) d 8.86 (dd, 1H), 8.34 (dd, 1H), 7.87 (d, 1H), 7.71 (dd, 1H), 7.48 (d, 1H), 7.24 (d, 1H), 3.96 (s, 3H), 3.35 (s, 3H). MS Chemical Formula: $C_{16}H_{13}N_3O$ calculated mass, 263.11, observed 264.1 (M+1).

Example 8

9-methoxy-6-propyl-6H-indolo[2,3-b][1,5]naphthyridine

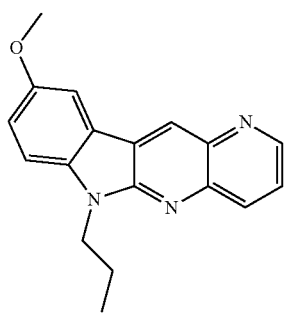 [SMILES: CCCn1c2ccc(OC)cc2c2cc3ncccc3nc21]

The compound was synthesized as shown in Preparative Example B above. Purification done using a Teledyne ISCO Combiflash on a silica support using hexanes: ethyl acetate gradient. HPLC run on Agilent 1100 using water w/0.1% Formic acid:Acetonitrile 95:5 to 100% MeCN over a ten minute gradient on phenomenex 75×4.6 mm C18 column. Rt: 7.6 minutes. $^1$H-NMR (400 MHz, CDCl3) δ 8.9 (m, 2H), 8.41 (d, 1H), 7.75 (d, 1H), 7.63 (dd, 1H), 7.39 (m, 1H), 7.25 (m, 1H), 4.45 (t, 2H), 3.98 (s, 3H), 2.00 (m, 2H), 1.03 (t, 3H). MS Chemical Formula: $C_{18}H_{17}N_3O$, calculated mass, 291.14. observed 292.2 (M+1).

Example 9

9,11-dimethyl-6-propyl-6H-indolo[2,3-b][1,5]naphthyridine

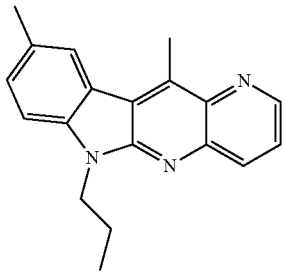 [SMILES: CCCn1c2ccc(C)cc2c2c(C)c3ncccc3nc21]

The compound was synthesized as shown in Preparative Example B above. Purification done using a Teledyne ISCO Combiflash on a silica support using hexanes: ethyl acetate gradient. HPLC run on Agilent 1100 using water w/0.1% Formic acid:Acetonitrile 95:5 to 100% MeCN over a ten minute gradient on phenomenex 75×4.6 mm C18 column. Rt: 9.9 minutes. $^1$H-NMR (400 MHz, CDCl3) δ 8.93 (dd, 1H), 8.44 (d, 1H), 8.15 (s, 1H), 7.63 (dd, 1H), 7.44 (d, 1H), 7.37 (d, 1H), 4.49 (d, 2H), 3.39 (s, 3H), 2.60 (s, 3H), 1.98 (m, 2H), 1.03 (t, 3H). MS Chemical Formula: $C_{19}H_{19}N_3$, calculated mass, 289.16. observed 290.1 (m+1).

Example 10

9-chloro-6-propyl-6H-indolo[2,3-b][1,5]naphthyridine

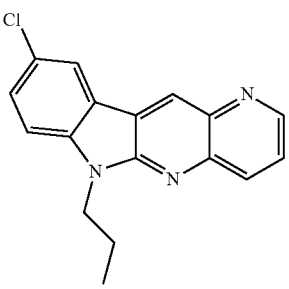 [SMILES: CCCn1c2ccc(Cl)cc2c2cc3ncccc3nc21]

The compound was synthesized as shown in Preparative Example B above. Purification done using a Teledyne ISCO Combiflash on a silica support using hexanes: ethyl acetate gradient. HPLC run on Agilent 1100 using water w/0.1% Formic acid:Acetonitrile 95:5 to 100% MeCN over a ten minute gradient on phenomenex 75×4.6 mm C18 column. Rt: 9.1 minutes. $^1$H-NMR (400 MHz, CDCl3) δ 8.93 (m, 2H), 8.45 (m, 1H), 8.20 (d, 1H), 7.65 (dd, 1H), 7.57 (dd, 1H), 7.40 (d, 1H), 4.52 (t, 2H), 2.0 (m, 2H), 1.03 (t, 3H). MS Chemical Formula: $C_{17}H_{14}ClN_3$, calculated mass, 295.09. observed 296.1 (M+1).

Example 11

7-chloro-10-propyl-10H-indolo[2,3-b][1,7]naphthyridine

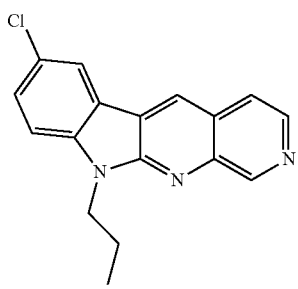 [SMILES: CCCn1c2ccc(Cl)cc2c2cc3ccncc3nc21]

The compound was synthesized as shown in Preparative Example B above. Purification done using a Teledyne ISCO Combiflash on a silica support using hexanes: ethyl acetate gradient. HPLC run on Agilent 1100 using water w/0.1% Formic acid:Acetonitrile 95:5 to 100% MeCN over a ten minute gradient on phenomenex 75×4.6 mm C18 column. Rt: 7.5 minutes. $^1$H-NMR (400 MHz, CDCl3) δ 9.56 (s, 1H), 8.75 (m, 1H), 8.54 (m, 1H), 8.21 (d, 1H), 8.0 (m, 1H), 7.65 (m, 1H), 7.45 (m, 1H), 4.52 (t, 2H), 2.0 (m, 2H), 1.03 (t, 3H). MS Chemical Formula: $C_{17}H_{14}ClN_3$, calculated mass, 295.09. observed 296.1 (m+1).

Example 12

9-methoxy-6H-indolo[2,3-b][1,5]naphthyridine

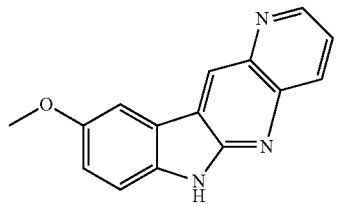 [SMILES: COc1ccc2[nH]c3nc4cccnc4cc3c2c1]

The compound was synthesized as shown in Preparative Example B above. Purification was done using preparative thin layer chromatography (dichloromethane/methanol 95:5). HPLC run on Agilent 1100 using water w/0.1% Formic acid:Acetonitrile 95:5 to 100% MeCN over a ten minute gradient on phenomenex 75×4.6 mm C18 column. Rt: 5.0 minutes. $^1$H-NMR (400 MHz, CD3OD) d 9.01 (s, 1H), 8.85 (dd, 1H) 8.43 (d, 1H), 7.87 (d, 1H), 7.75 (dd, 1H), 7.47 (d, 1H), 7.24 (dd, 1H), 3.96 (s, 3H). MS Chemical Formula: $C_{15}H_{11}N_3O$, calculated mass, 249.09. observed 250.1 (M+1)

Example 13

7-methoxy-10H-indolo[2,3-b][1,7]naphthyridine

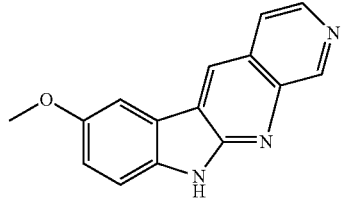 [SMILES: COc1ccc2[nH]c3nc4cnccc4cc3c2c1]

The compound was synthesized as shown in Preparative Example B above. Purification was done using preparative thin layer chromatography (dichloromethane/methanol 85:15). HPLC run on Agilent 1100 using water w/0.1% Formic acid:Acetonitrile 95:5 to 100% MeCN over a ten minute gradient on phenomenex 75×4.6 mm C18 column. Rt: 4.4 minutes. $^1$H-NMR (400 MHz, CD3OD) d 9.23 (s, 1H), 9.00 (s, 1H), 8.42 (d, 1H), 8.03 (d, 1H) 7.87 (s, 1H), 7.48 (d, 1H), 7.26 (dd, 1H), 3.95 (s, 3H). MS Chemical Formula: $C_{15}H_{11}N_3O$, calculated mass, 249.09. observed 250.1 (M+1).

Example 14

6H-indolo[2,3-b][1,5]naphthyridin-9-ol

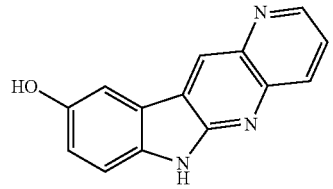 [SMILES: Oc1ccc2[nH]c3nc4cccnc4cc3c2c1]

The compound was synthesized as shown in Preparative Example B above. Purification done using a Teledyne ISCO Combiflash on a C18 support using a water:acetonitrile gradient. HPLC run on Agilent 1100 using water w/0.1% Formic acid:Acetonitrile 95:5 to 100% MeCN over a ten minute gradient on phenomenex 75×4.6 mm C18 column. Rt: 3.8 minutes. $^1$H-NMR (400 MHz, CD3OD) d 8.89 (s, 1H), 8.83 (dd, 1H), 8.40 (d, 1H), 7.73 (dd, 1H), 7.65 (d, 1H), 7.39 (d, 1H), 7.13 (dd, 1H). MS Chemical Formula: $C_{14}H_9N_3O$, calculated mass, 235.07. observed 236.1 (M+1).

Example 15

7-methoxy-6H-indolo[2,3-b][1,5]naphthyridine

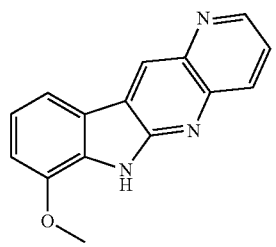 [SMILES: COc1cccc2c1[nH]c1nc3cccnc3cc12]

The compound was synthesized as shown in Preparative Example B above. Purification done using a Teledyne ISCO Combiflash on a C18 support using water:acetonitrile gradient. HPLC run on Agilent 1100 using water w/0.1% Formic acid:Acetonitrile 95:5 to 100% MeCN over a ten minute gradient on phenomenex 75×4.6 mm C18 column. Rt: 5.20 minutes. ¹H-NMR (400 MHz, CD3OD) d 8.89 (s, 1H), 8.87 (dd, 1H), 8.46 (dd, 1H), 7.89 (d, 1H), 7.75 (dd, 1H), 7.29 (dd, 1H), 7.21 (d, 1H), 4.08 (s, 3H). MS Chemical Formula: $C_{15}H_{11}N_3O$, calculated mass, 249.09. observed 250.1 (M+1).

Example 16

7-methoxy-10-propyl-10H-indolo[2,3-b][1,7]naphthyridine

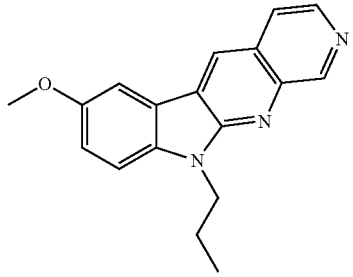 [SMILES: CCCn1c2ccc(OC)cc2c2cc3ccncc3nc21]

The compound was synthesized as shown in Preparative Example B above. Purification done using a Teledyne ISCO Combiflash on a silica support using hexanes: ethyl acetate gradient. HPLC run on Agilent 1100 using water w/0.1% Formic acid:Acetonitrile 95:5 to 100% MeCN over a ten minute gradient on phenomenex 75×4.6 mm C18 column. Rt: 6.04 minutes. ¹H-NMR (400 MHz, CDCl3) δ 9.54 (s, 1H), 8.63 (m, 1H), 8.51 (s, 1H), 7.78 (m, 1H), 7.66 (m, 1H), 7.37 (m, 1H), 7.25 (m, 1H), 4.46 (q, 2H), 3.95 (d, 3H), 1.97 (m, 2H), 1.01 (t, 3H). MS Chemical Formula: $C_{18}H_{17}N_3O$ calculated mass, 291.14. observed 292.2 (M+1).

Example 17

9-methyl-6H-indolo[2,3-b][1,5]naphthyridine

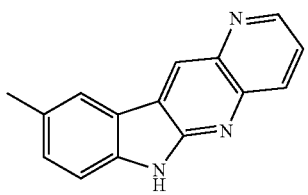 [SMILES: Cc1ccc2[nH]c3nc4cccnc4cc3c2c1]

The compound was synthesized as shown in Preparative Example B above. Purification done using a Teledyne ISCO Combiflash on a C18 support using water:acetonitrile gradient. HPLC run on Agilent 1100 using water w/0.1% Formic acid:Acetonitrile 95:5 to 100% MeCN over a ten minute gradient on phenomenex 75×4.6 mm C18 column. Rt: 5.5 minutes. ¹H-NMR (400 MHz, CDCl3) δ 9.15 (s, 1H), 8.98 (d, 1H), 8.55 (d, 1H), 8.01 (s, 1H), 7.74 (dd, 1H), 7.43 (s, 3H), 2.56 (s, 3H). MS Chemical Formula: $C_{15}H_{11}N_3$ calculated mass, 233.10. observed 234.1 (M+1).

Example 18

11-butyl-9-methoxy-6H-indolo[2,3-b][1,5]naphthyridine

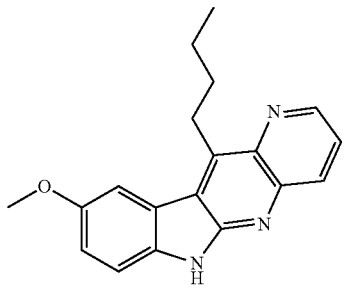 [SMILES: CCCCc1c2ncccc2nc2[nH]c3ccc(OC)cc3c12]

The compound was synthesized as shown in Preparative Example B above. Purification done using a Teledyne ISCO Combiflash on a C18 support using water:acetonitrile gradient. HPLC run on Agilent 1100 using water w/0.1% Formic acid:Acetonitrile 95:5 to 100% MeCN over a ten minute gradient on phenomenex 75×4.6 mm C18 column. Rt: 8.0 minutes. ¹H-NMR (400 MHz, CD3OD) d 8.85 (dd, 1H), 8.31 (dd, 1H), 7.73 (d, 1H), 7.69 (dd, 1H), 7.47 (d, 1H), 7.22 (dd, 1H), 3.99 (s, 3H), 3.86 (m, 2H), 1.86 (m, 2H), 1.67 (m, 2H), 1.07 (t, 3H). MS Chemical Formula: $C_{19}H_{19}N_3O$, calculated mass, 305.15. observed 306.2 (M+1).

Example 19

6-acetyl-6H-indolo[2,3-b][1,5]naphthyridin-9-yl acetate

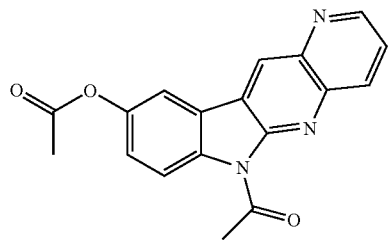 [SMILES: CC(=O)Oc1ccc2c(c1)c1cc3ncccc3nc1n2C(C)=O]

To a flask charged with 6H-indolo[2,3-b][1,5]naphthyridin-9-ol (0.02 grams, 0.085 mmol), was added DMAP (0.001 gram). The mixture was taken up in 0.9 mL of anhydrous DMF. While stirring at room temperature, triethylamine (0.023 mL, 0.17 mmol) was added followed by acetyl achloride (0.009 mL, 0.13 mmol). The next day, the reaction was diluted with methanol and concentrated. Purification was done using a Teledyne ISCO Combiflash on a C18 support using water w/0.1% formic acid:acetonitrile gradient. HPLC run on Agilent 1100 using water w/0.1% Formic acid:Acetonitrile 95:5 to 100% MeCN over a ten minute gradient on phenomenex 75×4.6 mm C18 column. Rt: 7.5 minutes. ¹H-NMR (400 MHz, CD3OD) d 9.00 (m, 2H), 8.72 (d, 1H), 8.56 (dd, 1H), 8.09 (d, 1H), 7.82 (dd, 1H), 7.38 (dd, 1H), 3.26 (s, 3H), 2.37 (s, 3H). MS Chemical Formula: $C_{18}H_{13}N_3O_3$, calculated mass, 319.10. observed 320.2 (M+1).

Example 20

9-(trifluoromethoxy)-6H-indolo[2,3-b][1,5]naphthyridine

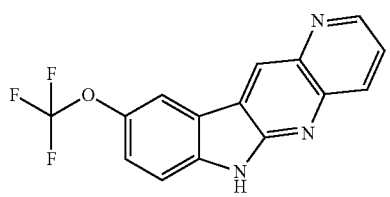 [SMILES: FC(F)(F)Oc1ccc2[nH]c3nc4cccnc4cc3c2c1]

The compound was synthesized as shown in Preparative Example B above. Purification done using a Teledyne ISCO Combiflash on a C18 support using water:acetonitrile gradient. HPLC run on Agilent 1100 using water w/0.1% Formic acid:Acetonitrile 95:5 to 100% MeCN over a ten minute gradient on phenomenex 75×4.6 mm C18 column. Rt: 6.9 minutes. $^1$H-NMR (400 MHz, CD3OD) d 9.11 (s, 1H), 8.89 (dd, 1H), 8.46 (d, 1H), 8.29 (d, 1H), 7.77 (dd, 1H), 7.61 (d, 1H), 7.53 (dd, 1H). MS Chemical Formula: $C_{15}H_8F_3N_3O$, calculated mass, 303.06. observed 304.1 (M+1).

Example 21

Biological Assay

Human mammary cancer MCF-7 cells were maintained under standard conditions using Dulbecco's Modified Eagle Medium Nutrient Mixture F12 (DMEM-F12, GIBCO #12400-024) accompanied by 10% fetal calf serum (FCS, Atlanta Biologicals #S 11550). Cells were cultured to 80% confluency before being lifted with 0.05% Trypsin/EDTA (GIBCO #1404912) for 2 minutes, spun and resuspended in new media.

MCF7 cells were seeded at a density of 10,000 cells per well in 96 well plates (BD Falcon #353220). Cells were grown for 24 h, washed in phosphate-buffered saline (PBS, Life Technologies #14080-055), media was then replaced with DMEM-F12 at 5% FCS. At this time Ellipticine, including Aza-Ellipticine compounds, were added from a treatment plate (3 µL per condition) for a total volume of 150 µL (final concentrations of 0.1, 1, 3, 10 µM) and were incubated under standard conditions for an additional 72 h.

After 72 h of treatment with drugs, cells were fixed by adding 50 µL of 10% Buffered Formalin Phosphate and stained with 2 µM Hoechst 33342 (AnaSpec #83218) stock (20000×) to media for 1 h. Images were then captured with the IN Cell Analyzer 2000 (GE Healthcare UK Ltd., Buckinghamshire, UK).

$EC_{50}$ values for representative compounds of the invention are shown in the table below:

| Example | Compound | Cytotoxicity, $EC_{50}$ |
|---|---|---|
| 8 | | 13.3 µM |
| 17 | | 900 nM |
| 18 | | 1 µM |
| 19 | | 1 µM |
| 7 | | 14 µM |
| 12 | | 800 nM |

| Example | Compound | Cytotoxicity, EC$_{50}$ |
|---|---|---|
| 13 | (structure) | 17 µM |
| 2 | (structure) | 6 µM |
| 14 | (structure) | 5 µM |
| 15 | (structure) | No effect |
| | ellipticine | 1 µM |
| | 9-Hydroxy ellipticine | 900 nM |

All of the compounds, compositions and methods disclosed and claimed herein can be made and executed without undue experimentation in light of the present disclosure. While the disclosure may have only been described in terms of certain embodiments, it will be apparent to those of skill in the art that variations may be applied to the compounds, compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

Handbook of Pharmaceutical Salts: Properties, and Use, Stahl and Wermuth Eds., Verlag Helvetica Chimica Acta, 2002.

March's Advanced Organic Chemistry: Reactions, Mechanisms, and Structure, 2007.

Mathe, et al., Biomedicine & Pharmacotherapy, 52(9):391-396, 1998.

Pohlit, et al., Phytomedicine, 19(11):1049, 2012.

Ramkumar and Nagarajan, Tetrahedron Letters, 55:1104-1106, 2014.

Stiborova, et al., Current Medicinal Chemistry, 19(25): 4218-4238, 2012.

Zhang, et al., J. Org. Chem., 65(23):7977-7983, 2000.

What is claimed is:

1. A compound, wherein the compound is:
   6H-indolo[2,3-b][1,5]naphthyridine;
   6-propyl-6H-indolo[2,3-b][1,5]naphthyridine;
   10-propyl-10H-indolo[2,3-b][1,7]naphthyridine;
   9-methyl-6-propyl-6H-indolo[2,3-b][1,5]naphthyridine;
   7-methyl-10-propyl-10H-indolo[2,3-b][1,7]naphthyridine;
   9-methoxy-6-propyl-6H-indolo[2,3-b][1,5]naphthyridine;
   9,11-dimethyl-6-propyl-6H-indolo[2,3-b][1,5]naphthyridine;
   9-chloro-6-propyl-6H-indolo[2,3-b][1,5]naphthyridine;
   7-chloro-10-propyl-10H-indolo[2,3-b][1,7]naphthyridine;
   9-methoxy-6H-indolo[2,3-b][1,5]naphthyridine;
   7-methoxy-10H-indolo[2,3-b][1,7]naphthyridine;
   6H-indolo[2,3-b][1,5]naphthyridin-9-ol;
   7-methoxy-6H-indolo[2,3-b][1,5]naphthyridine;
   7-methoxy-10-propyl-10H-indolo[2,3-b][1,7]naphthyridine;
   9-methyl-6H-indolo[2,3-b][1,5]naphthyridine;
   11-butyl-9-methoxy-6H-indolo[2,3-b][1,5]naphthyridine;
   6-acetyl-6H-indolo[2,3-b][1,5]naphthyridin-9-yl acetate; or
   9-(trifluoromethoxy)-6H-indolo[2,3-b][1,5]naphthyridine,
   or a pharmaceutically acceptable salt or tautomer thereof.

2. A pharmaceutical composition, comprising a compound according to claim 1, or at pharmaceutically acceptable salt or tautomer thereof, and an excipient.

* * * * *

UNITED STATES PATENT AND TRADEMARK OFFICE
CERTIFICATE OF CORRECTION

PATENT NO. : 10,456,400 B2
APPLICATION NO. : 15/307966
DATED : October 29, 2019
INVENTOR(S) : Christopher C. Lindsey et al.

It is certified that error appears in the above-identified patent and that said Letters Patent is hereby corrected as shown below:

In the Claims

At Column 52, Lines 52-53, "or at pharmaceutically acceptable salt" should be replaced with "or a pharmaceutically acceptable salt."

Signed and Sealed this
Twenty-fifth Day of February, 2020

Andrei Iancu
*Director of the United States Patent and Trademark Office*